(12) United States Patent
Brady et al.

(10) Patent No.: US 11,298,375 B2
(45) Date of Patent: Apr. 12, 2022

(54) HALOGENATED FULLERENE FUNCTIONALIZED AS A BIOCIDAL AND CHEMOTACTIC SPERMICIDE TO VAGINALLY HARBOR AND NEUTRALIZE SPERMATOZOA FOR USE AS A SAFE AND EFFECTIVE CONTRACEPTIVE

(71) Applicants: Terry Earl Brady, The Valley (AL); Anthony Lee Dellinger, Brown Summit, NC (US); Melinda K. M. Goddard, The Valley (AL); Kristen Dellinger, Brown Summit, NC (US)

(72) Inventors: Terry Earl Brady, The Valley (AL); Anthony Lee Dellinger, Brown Summit, NC (US); Melinda K. M. Goddard, The Valley (AL); Kristen Dellinger, Brown Summit, NC (US)

( * ) Notice: Subject to any disclaimer, the term of this patent is extended or adjusted under 35 U.S.C. 154(b) by 0 days.

(21) Appl. No.: 17/499,223

(22) Filed: Oct. 12, 2021

(65) Prior Publication Data

US 2022/0047629 A1 Feb. 17, 2022

(51) Int. Cl.
*A61K 33/44* (2006.01)
*A61K 31/11* (2006.01)
(Continued)

(52) U.S. Cl.
CPC ............ *A61K 33/44* (2013.01); *A61K 9/0034* (2013.01); *A61K 9/02* (2013.01); *A61K 31/11* (2013.01); *A61K 31/57* (2013.01); *A61K 38/1703* (2013.01)

(58) Field of Classification Search
CPC ...................................................... A61K 33/44
See application file for complete search history.

(56) References Cited

U.S. PATENT DOCUMENTS 4,589,880 A * 5/1986 Dunn .................... A61K 9/0036
128/832
10,934,168 B1 * 3/2021 Brady ..................... D06M 11/74
(Continued)

FOREIGN PATENT DOCUMENTS

CN 104984347 A * 10/2015
WO WO-2004033496 A1 * 4/2004 ............. A61K 31/11

OTHER PUBLICATIONS

Google Patents. English Translation of WO2004033496A1. Obtained from https://patents.google.com/patent/WO2004033496A1/en?oq=WO+2004033496 on Jan. 5, 2022, originally published 2004, pp. 1-24. (Year: 2004).*

(Continued)

*Primary Examiner* — Isaac Shomer (57) ABSTRACT

The present invention provides the methods and composition useful as a contraceptive by preventing motile sperm from reaching a mature ovum, thereby blocking fertilization and preventing pregnancy. The contraceptive is comprised of halogen functionalized fullerene nanoparticles (halo fullerenes) and chemotactic stimulants that act synergistically to divert, incapacitate and ultimately rupture spermatozoa to avert fertilization. When applied vaginally prior to coitus, the suspension is activated by exposure to spermatozoa upon insemination. Notably, non-spermatozoa cells are unaffected by the pH-neutral suspension; however, closer to the same scale, microbes are susceptible to its inherent biocidal properties. Following application and coitus, the contraceptive evacuates naturally, along with seminal and vaginal fluids thereafter.

19 Claims, 2 Drawing Sheets

(51) Int. Cl.
*A61K 9/02* (2006.01)
*A61K 38/17* (2006.01)
*A61K 31/57* (2006.01)
*A61K 9/00* (2006.01)

(56) References Cited

U.S. PATENT DOCUMENTS

2011/0270127 A1* 11/2011 Vered ............... A61B 10/0096
600/573
2015/0359737 A1* 12/2015 Bernick ................ A61K 9/02
424/452
2016/0289735 A1* 10/2016 Gerdes ................ G01N 33/689

OTHER PUBLICATIONS

Google Patents. English Translation of CN104984347A. Obtained from https://patents.google.com/patent/CN104984347A/en?oq=CN+104984347 on Jan. 5, 2022. Originally published 2015, pp. 1-7. (Year: 2015).*

Scitechnology Scientific Journal. https://scitechnology.ru/wp-content/uploads/2018/05/Sci-%D1%80%D0%BD%D0%B0%D0%BB-16.pdf#page=9 accessed Jan. 2, 2021, originally published 2018, pp. 1-80. (Year: 2018).*

* cited by examiner

HALOGENATED FULLERENE FUNCTIONALIZED AS A BIOCIDAL AND CHEMOTACTIC SPERMICIDE TO VAGINALLY HARBOR AND NEUTRALIZE SPERMATOZOA FOR USE AS A SAFE AND EFFECTIVE CONTRACEPTIVE

CROSS REFERENCE TO RELATED APPLICATION(S)

NA.

BACKGROUND OF THE INVENTION

Field of the Invention

This invention relates to a contraceptive suspension comprised of halo fullerenes and chemosensory stimulants and methods for formulation and use. The contraceptive suspension diverts chemoattractant targeting, impedes spermatozoa motility, and destroys cellular integrity to preclude access to and fertilization of a mature ovum through multiple mechanisms.

Description of Related Art

This patent follows U.S. Pat. No. 10,934,168, which describes a synthetic, halogenated, functionalized fullerene engineered for biocidal effect. The halo fullerene is physically and caustically destructive to microbial organisms but neutral with respect to larger mammalian cells and tissues. The functionalized fullerene in U.S. Pat. No. 10,934,168 can be applied to barrier garments, accessory garments (including, but not limited to shoe covers, masks, and facial visors), textiles (including, but not limited to bed sheets, blankets, towels, personal clothing, gowns, surgical drapes, curtains, and pads), filtration matrices (e.g. for use in hemodialysis and hemofiltration), or an aerosolized solution, spray, liquid, salve, or cream. In U.S. Pat. No. 10,934,168, impregnation of the halo fullerenes into an article establishes a resilient and enduring bioactive coating with antimicrobial properties that inhibits growth and proliferation of microbes by rupturing their cellular membranes.

This Application illustrates another embodiment of the invention described in U.S. Pat. No. 10,934,168 in the form of a contraceptive suspension and method for formulation using synthetic, halogenated, functionalized fullerenes not previously disclosed. In the preferred embodiment, the formulation combines halo fullerenes with chemotactic analytes that combine to divert, rupture and incapacitate spermatozoa. In the first instance, the relative size of the spermatozoa approximate that of many microbes, making them uniquely susceptible to the physical dynamics described in U.S. Pat. No. 10,934,168 with respect to biocidal effects; whereby, halo fullerenes accelerate when agitated in the vortexes trailing sperm motility so as to bombard the spermatozoa, with particular impact on the distal tail section that is most vulnerable to rupture from contact with caustic halogen sites on the functionalized fullerenes, as described in U.S. Pat. No. 10,934,168. The physical rupture of the sperm cells is facilitated by leveraging additional properties of sperm activity including: chemotactic receptors that orient the sperm toward attractants on the surface of a mature ovum, as well as receptors that initiate well characterized aggression in the presence of competitive ejaculate.

By including synthetic and biological materials to mimic the ovum and competitive semen, this embodiment essentially harbors the sperm in a zone of attractants as a diversion from advancing toward an actual mature ovum, if present. In turn, the competitive molecules stimulate aggressive interactions between the spermatozoa, further diverting them from progression beyond the vaginal cul-de-sac. In response, the spermatozoa expend inordinate amounts of energy otherwise required for continuing into the uterus and on to a fallopian tube, where fertilization could then be achieved. This accelerated motility and propulsion thereby intensify the cellular impact and consequent rupture from concentrated exposure to the halo fullerenes as a spermicidal contraceptive mechanism.

Notably, contraception, fertility and childbearing have intersected at the crossroads of culture, biology, religion, economy, technology, and laws around the world since time immemorial. Some of the first references to understanding and managing the cycles of human fertility date back to 1850 BC in ancient Egypt [Cuomo, 2010; Lipsey et al., 2005]. Indeed, a myriad of cultural norms can also be traced to religious scriptures and dogma that defined and dictated the roles for childbearing women and the men whose property or power may have been vested in their offspring. [Freedman and Isaacs, 1993] As such, the quest for reproductive choice and the political and economic rights it enables has spanned centuries as an ongoing work in progress to this day [Sommer and Forman-Rabinovici, 2019].

In fact, 99% of sexually active, biological women in the United States currently report having used some form of contraception, and 87.5% have reported using highly effective, reversible methods [American College of Obstetricians and Gynecologists, 2015]. However, demanding pill schedules, complicated or unreliable devices, side effects including unwanted pregnancy, cost, access, and lack of confidentiality can pose challenges to efficacy and consistent compliance. Considered by the Centers for Disease Control and Prevention as one of the ten most important public health achievements of the 20th century, contraceptives have: improved human health and well-being; reduced maternal mortality while helping optimize family planning; and enabled significant advances in female workforce productivity and independence, among an array of economic and health benefits not possible in the absence of reproductive choice [Public Health Service, 1994].

Where the law and culture have afforded reproductive rights, technological boundaries have still fallen short of absolute efficacy. While the most accepted methods of hormonal intervention (i.e. oral contraceptives) are highly effective, the correspondingly common alternatives of traditional spermicide and condoms typically yield some 80% efficacy in pregnancy prevention [Bryant-Comstock, et al., 2016]. Nonetheless, contraceptive failure has been primarily attributed to compliance issues impacting all methods (e.g. missed pill, dislodged device, ruptured condoms, etc.) [Grimes, 2009]; such failures might actually be far more frequent, but for an overall 30% probability of unprotected intercourse yielding successful fertilization of a mature ovum [American Pregnancy Association, 2021].

To date, most contraceptive developments have focused on female hormonal interventions to prevent access to mature ova, and thus, fertilization. That said, the fragility and imperfections of spermatozoa present a uniquely opportunistic pathway to contraception, as these cells can be controlled with significantly fewer side-effects when compared to hormonal oral and implantable methods. Specifically, 4-10% of human sperm are typically viable in any given ejaculate sample [Helo, 2020] with an average of approximately 40% motility across the specimen [Healthline, 2018]. In addition to a broad normal range of sperm counts, dysmorphic spermatozoa have also been observed to include: multiple or tiny heads; oversized heads; multiple or absence of tails; and weak or absent motility [Helo, 2020]. As such, spermatozoa vulnerabilities appear to warrant more contraceptive focus and innovation.

Condoms, the most common of the latter contraceptive embodiments, function as a barrier for semen and sperm, but their utility poses many shortcomings. In addition to failures from unintended tears or slippage, reports of non-consensual removal have compromised female reproductive choices [Davis, 2019]. These issues have underpinned the widespread adoption of female-directed contraception using oral, transdermal and implantable hormones, intrauterine (IUD) or diaphragm devices, and traditional spermicides. However, such choices have nonetheless been limited by the constraints of legal, cultural, financial, and technology access, as well as efficacy and tolerance of side effects, as noted previously. In particular, hormonal, and both intrauterine (insertion) and diaphragm (fitting and instruction) device options, may pose access and financial issues by requiring a clinician to prescribe, insert or otherwise fit such female-directed choices.

While hormone-based methods have been proven generally reliable, numerous complications and side effects have been associated with prolonged use [Wright and Johnson, 2008], along with the risks of noncompliance with daily administration and resulting loss of efficacy for oral contraceptives. Specifically, hormonal contraceptives have been associated with: dermatological conditions; fatigue; migraines; anxiety and depression; tenderness and enlargement of breasts; altered appetite; bloating and nausea; weight fluctuations; vaginal irritation; blood pressure changes; and hirsutism [FDA, 2005]. Implantable forms have also reportedly caused: abdominal and back pain; benign ovarian cysts; alteration of duration and volume and/or cessation of menstruation; decreased libido; vertigo; insulin resistance; and vaginal inflammation and dryness [Shazly and Laughlin-Tommaso, 2020]. While injectable and transdermal hormone-based methods mitigate the rigors of compliance, these have demonstrated more severe and more frequent side-effects than the oral and implantable options [Moses-Kolko et al., 2009].

Once properly inserted, intrauterine devices (IUDs) have been shown to match the efficacy of hormone contraceptives, but they pose yet other risks, including uterine perforation, infection, intense cramping, irregular periods, heavy bleeding and/or random spotting [Chakraborty, et al., 2015]. In addition to perforation, insertion complications also include pain, irritation, swelling, bruising, numbness, tingling and infection [Farmer and Webb, 2003]. Secondary to this procedure, scar tissue may also form around the implant, making removal problematic; conversely, some devices have reportedly been asymptomatically expelled or migrated after insertion [Boortz et al., 2012].

With respect to traditional spermicides, efficacy remains a major limitation, with leading products in the category claiming 80% effectiveness if used as directed [Cornell Health, 2019]. The active ingredients in most of these are surfactants, notably nonoxynol-9 [CDC, 2002]. While spermicides contain extremely potent immobilizing agents, common issues include sperm evasion and irritation of the vaginal tissues from acute pH shifts, especially associated with nonoxynol-9 formulations [Stafford, et al., 1998].

Given this spectrum of issues spanning cost, access to reproductive healthcare, metabolic and physical side effects, and compliance risks, new contraceptive approaches remain a global priority. Balancing the vulnerabilities of spermatozoa with the need for a female-directed method suggests an unmet need for a contraceptive that would match the control and efficacy of hormonal and intrauterine methods and the access, cost and safety profile of condoms and traditional spermicides when used as directed.

The US Department of Health and Human Services (HHS) has calculated that as many as 50% of all pregnancies are unintended [Aztlan-James, et al., 2017], and it has been estimated that as many as 1 of 4 women have had or will have an abortion by age 45 in the US [Jones and Jerman, 2017]. In the absence of effective and appropriate contraceptive methods, the HHS has set forth a national priority (described in the Healthy People 2020 goal) to reduce the unplanned pregnancy rate to 44% [US Dept. of Health and Human Services, 2010]. Still, many women and their partners struggle with the medical, ethical, social, legal, and financial challenges associated with its occurrence. As a consequence, on a national scale, the US government and taxpayer burden for related medical and social services for early child care is more than $20 billion per year, including hospitalizations for labor and delivery [Sonfield and Kost, 2015].

As reported herein, the Applicants have applied invention associated with U.S. Pat. No. 10,934,168 and claim that the halo fullerenes in combination with chemosensory stimulants represent a novel contraceptive that is safe, effective, easy to use, accessible, and discreet. As such, the invention would match the female control and efficacy of hormonal and intrauterine methods and the access, cost and safety profile of condoms and traditional spermicides when used as directed.

BRIEF SUMMARY OF THE INVENTION

The primary object of the present invention leverages the scale of spermatozoa and infectious pathogens relative to that of nanoparticles, as both are susceptible to cellular rupture by contact with halogenated, functionalized fullerenes, as described in U.S. Pat. No. 10,934,168. This innovation combines halo fullerenes with chemotactic additives for use as a contraceptive based on three redundant mechanisms: These prevent fertilization by chemotactically diverting and harboring active sperm in the vaginal cul-de-sac, away from a mature ovum, if present; second, by mimicking competitive ejaculate to stimulate agitation; and thereby maximize contact with the halo fullerenes to physically rupture and incapacitate the spermatozoa at the atomic scale. The invention is thus a safe, non-hormonal contraceptive, which results in rapid spermatozoa diversion, rupture and incapacitation with a low dose of active ingredients in a neutral-pH, non-irritating suspension consistent with vaginal homeostasis. The present invention is administered vaginally using a simple syringe and plunger or insertion of a suppository that quickly dissolves at normal body temperature, releasing the contraceptive suspension.

Highly specific to mammalian spermatozoa due to their size, the halo fullerenes accelerate when agitated in the vortexes trailing sperm motility, with particular effect on the most vulnerable distal tail section. As such, these dynamics intensify cellular contact with the caustic halogen sites on the fullerenes as described in U.S. Pat. No. 10,934,168 with respect to biocidal effects. The addition of synthetic and biologically safe chemotactic materials that mimic the ovum and competitive semen further enable this innovation to divert and to stimulate antagonistic interactions between the spermatozoa to maximize velocity of fullerene propulsion and therefore, efficacy.

With respect to the formulation, three active components are combined in a neutral-pH suspension including, but not limited to: (1) halo fullerenes; (2) bourgeonal, an aromatic aldehyde to mimic a mature ovum, as a spermatozoa attractant; (3) protamine, a chemotactic trigger to mimic competitive ejaculate, as a spermatozoa stimulant.

The present invention is comprised of active ingredients that can be produced cost-effectively, and that are highly specific, safe, stable, and effective.

An important object of the invention is to provide an accessible, affordable female-directed contraceptive in a discreet, culturally acceptable form with the efficacy of hormone-based methods and the safety profile of prophylactics and traditional spermicides.

A secondary, opportunistic object of the invention builds on the antimicrobial properties of the halo fullerenes as described in U.S. Pat. No. 10,934,168 with potential application for treatment and/or prevention of sexually transmitted infections of microbial origin.

DETAILED DESCRIPTION OF THE INVENTION

Figure 2A:
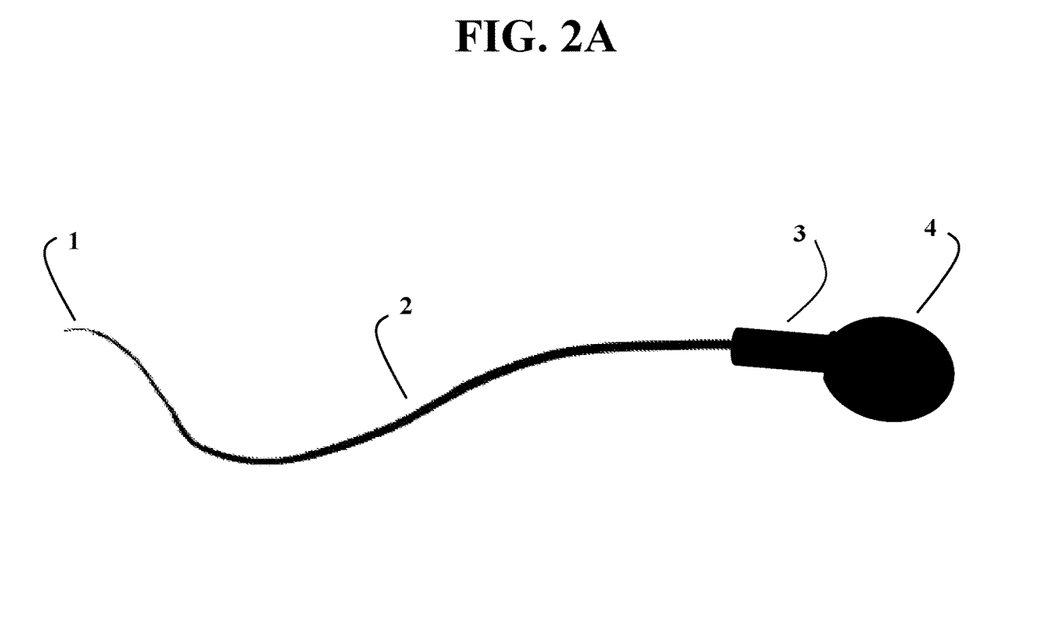
FIG. 2A is an illustration of a human spermatozoa and major sections of the cell; the distal or end piece 1, the principal piece 2, the mid-piece 3, and the head 4.
Figure 2B:
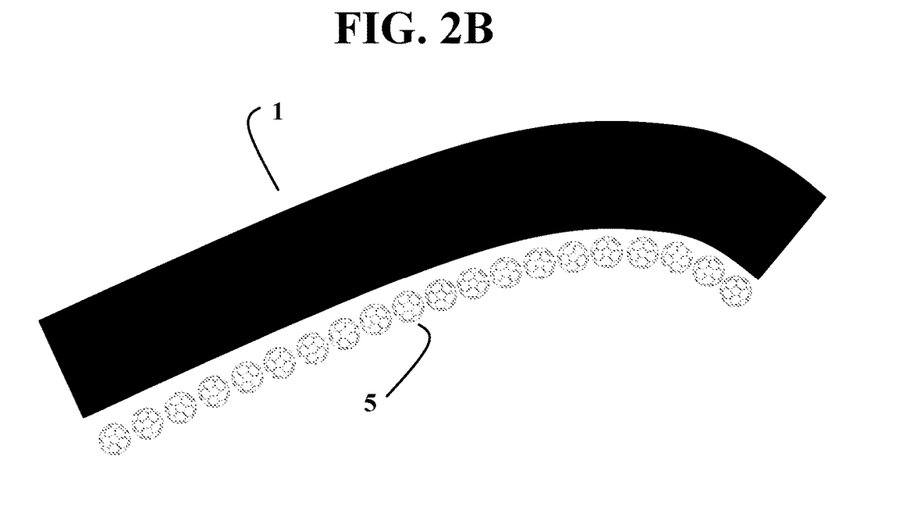
FIG. 2B is a representation of the arrangement of halogenated fullerene particles 5 alongside an exploded view of the distal or end tail portion 1 of a spermatozoa cell.

Spermatozoa represent the tiniest cell type in mammalian biology, and proportionately, fullerenes have mass comparable to the smallest aspect of spermatozoa, the distal tail segment 1 that propels them. The primary component of the proposed invention is a halogen modified fullerene 5, as described in U.S. Pat. No. 10,934,168.

The proposed invention would prevent fertilization following introduction of viable sperm into the vaginal tract and divert its otherwise normal progress through the cervix; whereby, it would have been propelled by chemotactic stimuli and attraction, through the uterine cavity and into a fallopian tube for sperm contact and penetration of a mature ovum, if present. Although the halo fullerenes remain neutral in the absence of spermatozoa introduction, in use, immediate halo fullerene and sperm interactions would occur as a result of unimpeded movement of both masses through the viscous, mucous phase of seminal fluid due to the large space between water molecules (vibrational excitation). The invention formulation would thus prevent fertilization; in the first instance, with substances that stimulate sperm receptors by mimicking the attractant of the mature ovum to divert them from cervical passage, essentially pooling them in the vaginal cul-de-sac. This diversion would then afford yet more agitation from a second mechanism mimicking competitive ejaculate. In turn, the third, yet most lethal, mechanism would result from the magnetic field generated by the spermatozoa flagella excitation that would further intensify velocity and rotation of the halo fullerenes at the atomic scale. This combined, hyperactivation of the sperm would thus propel an overwhelming barrage of halo fullerenes 5 traveling at maximum velocities into the distal flagella 1, thereby rupturing and causing mitochondrial leakage throughout the ejaculate.

Figure 1A:
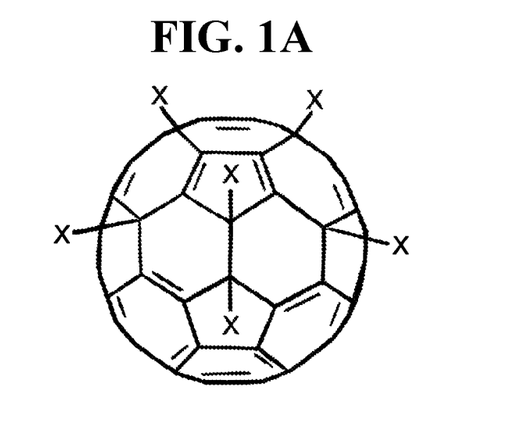
FIGS. 1A, 1B, and 1C are molecular representations of prototypical halo fullerenes of 60 carbon atoms functionalized with 4, 8, or 24 halogens (X).
Figure 1B:
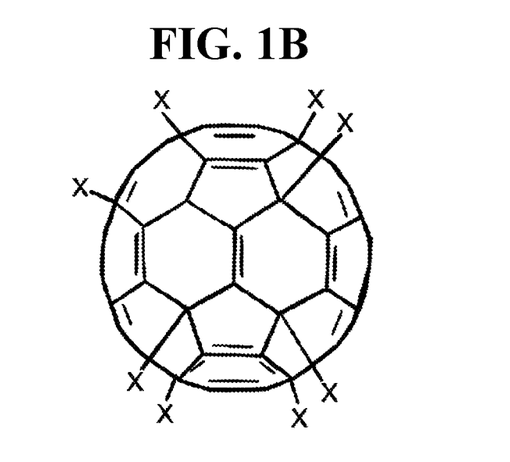
Figure 1C:
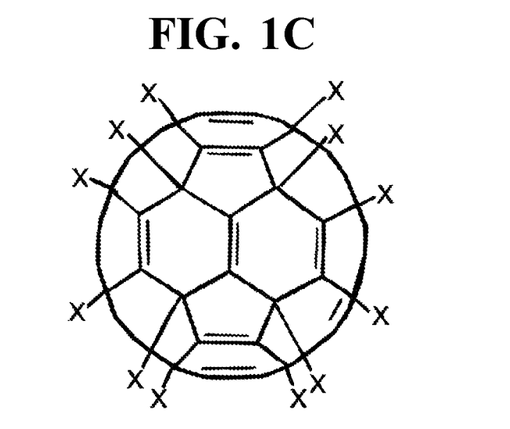

A broad range of carbon shell fullerene modifications have been demonstrated via numerous, well-described chemical reactions [Yan, et al., 2015]. In U.S. Pat. No. 10,934,168, a halogenated fullerene was comprised of a fullerene shell of $C_{2n}$; whereby, n=10, 12, 13, 14, 15, . . . 360, such that multiple side-chain halogens attached to the core carbon cage. U.S. Pat. No. 10,934,168 described three carbon-60 halo fullerenes of $C_{60}X_6$; $C_{60}X_8$, and $C_{60}X_{24}$; whereby, X=a halogen molecule (e.g. bromine, chlorine, iodine, and fluorine).

Halogen atoms are hydrophobic and lipophilic, which may be exploited for countless useful applications. Lipophilicity enables halogens to cross and pass through cell membranes. In U.S. Pat. No. 10,934,168, the halogen functional group applies these highly caustic atomic properties that induce cell rupture and destruction of vulnerable microbes, without a net loss of energy or efficacy, sustaining caustic capabilities at the application or exposure site. Hence, the contraceptive formulation could also prove effective against pathogen transmission.

The heads 4 of spermatozoa are highly variable (width and length), and the flagella can be divided into four segments: the connecting piece or neck; the mid-piece 3, the principal piece 2 and the distal or end piece 1. The connecting piece is adjacent to the head 4 and contains degenerated centrioles and transitional structures linked with the mid-piece, which is differentiated from the other segments by a cytoskeletal structure surrounded by mitochondria. The mitochondria produce adenosine triphosphate (ATP), which is transported from the mid-piece to the axonemal section, creating the energy required for motility of the sperm. The principal piece has a distinct fibrous sheath that surrounds the cytoskeletal structure. However, unlike the other segments, the end piece 1 is the most exposed region, lacking ancillary structures.

In this Application, protruding halogen sidechain(s) of the fullerenes are thus applied so as to compromise spermatozoa cell membrane integrity, which is directly related to motility, viability of attractant receptors, ovum penetration capability (capacitation) and overall osmotic equilibrium. The atomic size of halo fullerenes 5 makes these molecules particularly destructive to flagella end-piece segments 1. Similarly, specific regions of the sperm remain unaffected by the fullerene 5, including the larger head 4 section and the more structurally robust connecting, principal 2, and mid-piece 3 regions of the flagellum. Such scale disparities also prevent fullerene-induced damage to other larger cells. Yet, as noted, membrane damage to the distal flagellum 1 disables spermatozoa by rupture and intracellular fluid loss. Ideal formulation ratios of halo fullerenes in the suspension would thus significantly outnumber total spermatozoa counts, with multiple halogens around each fullerene for numerous contact points. Thus, spermatozoa rupture, structural damage, and immobilization would prevent fertilization before the seminal fluid liquidation phase.

Notably, spermatozoa cellular membranes are comprised primarily of poly-unsaturated fatty acids (PUFAs); these provide the fluidity and flexibility required for fertilization; but they also make spermatozoa vulnerable to free radical damage and initiation of the lipid peroxidation (LPO) cascade. The LPO cascade is an autocatalytic and self-propagating chain reaction directly associated with degradation.

For instance, LPO results in a rapid loss of intracellular ATP, which weakens the axial filament of spermatozoa and diminishes motility. Excessive LPO-based membrane impact can also lead to diminished morphological integrity and apoptosis. These consequences are exacerbated by halo fullerenes.

As such, spermatozoa cellular membranes are highly susceptible to peroxidation changes, which can directly impair motility and zona pellucida binding, or capacitation. Thus, an abundance of free radicals can cause deleterious cellular oxidation that induces structural and functional changes. Peroxidation-mediated damage to spermatozoa represents a key contributing factor in 30-80% of male infertility [O'Flaherty, 2020]. In particular, halo fullerene induced lipid peroxidation results in a chain reaction that produces reactive oxygen species (ROS).

The effect on fertility by ROS, as cellular by-products of reactions, is well documented [O'Flaherty, 2020]; whereby, all cellular components are targets for ROS-induced oxidative stress. In spermatozoa, ROS has been shown to trigger hyperactivation, capacitation, and initiation of the acrosome response, which are critical physiological processes necessary for fertilization. Thus, maintaining appropriate ROS equilibrium is essential for adequate spermatozoa functionality. Conversely, ROS excess adversely effects the cell membrane, DNA, and physiological processes of sperm.

In addition to the caustic properties of the halo fullerenes in the proposed invention, two spermatozoa-specific chemosensory mechanisms are applied. The chemotactic chemistry of the preferred embodiment includes 3-(4-tert-Butylphenyl) propanol (bourgeonal) and protamine. Notably, protamine has been used medically for decades as a heparin antagonist in the blood and is considered as a safe biological substance [Gurses, et al., 2015].

In the proposed invention, bourgeonal ($C_{13}H_{18}O$), an aromatic aldehyde odorant, is added to the contraceptive suspension to act as a powerful chemo-attractant and stimulant for spermatozoa [Olsson and Laska, 2010]. Bourgeonal is a potent agonist of the human sperm olfactory receptor OR1D2, which governs chemical communication between the sperm and ovum [Olsson and Laska, 2010]. Bourgeonal activation of OR1D2 results in the opening of calcium ion channels in the sperm that both enhance the speed and targeting of sperm motility [Veitinger et al., 2011]. The affinity and activation of bourgeonal and OR1D2 have been associated with species-specific fertilization [Spehr et al., 2006]. Bourgeonal is also linked to calcium-dependent signaling pathways controlled by the plasma membrane $Ca^{2+}$-ATPase (PMCA) transport system on the cell membrane [Yoshida et al., 2013]. PMCA is known to regulate calcium concentrations and homeostasis, which are essential for controlling the flagellar whipping, motility regulation, targeting, hyperactivation, zona pellucida binding, and the acrosome reaction. [Yoshida et al., 2013]. In the proposed invention, alternative sperm activating and attracting factors include analogues of bourgeonal, such as Helional, or other aromatic aldehydes, and aliphatic esters, such as n-pentyl acetate.

The third active component of the proposed invention is protamine. Whereby, human protamine is contained in the sperm head with its structure and size directly related to protamine levels and ratios. Human spermatozoa also have substantial OR1D2 receptors that have appeared to play an evolutionary role associated with exposure to competitive sperm from multiple partners [Eisenbach and Giojalas, 2006]. As such, a uniquely aggressive response has been observed between spermatozoa of two or more different males, reflecting a capacity to recognize self and non-self, which has been characterized in numerous species, including mammals [Andersson and Simmons, 2006]. Thus, the addition of protamine from any other source provides a tertiary contraceptive mechanism as a membrane binding and disruptive agent—and as an antagonist to stimulate the spermatozoa.

Already primed by the addition of bourgeonal to effect a synthetic chemosensory gradient resembling a proximal mature ovum, this competitive stimulant induces hyperactivation that appears to exhaust sperm motility. These behaviors produce greater ATP levels, which enables further acceleration of the flagella and thereby, increased motility and velocity. Spermatozoa and protamine interactions result in electrostatic membrane binding that coats the sperm and drives an aggressive and confrontational response, including between cells originating from a single source.

Given the application of the proposed invention suspension at an optimized ratio of halo fullerenes to the upper range of average sperm count levels, the ATP-induced increases in flagella velocity would likewise increase the speed and rotation of the halo fullerenes, exponentially increasing the incidence of halogen collisions and ruptures of the spermatozoa cellular membranes. This mechanism thus enhances the invention contraceptive efficacy by ATP depletion, structural damage, mitochondrial leakage, and lost motility prior to entering the cervix or uterus.

As spermatozoa mature, their membrane also undergoes surface remodeling that encapsulates the sperm in a glycocalyx layer, which carries a net negative charge [Simon et al., 2016]. About 94% of ejaculated sperm is negatively charged [Simon et al., 2016]. Cationic protamine and anionic sperm contact are governed by electrostatic interactions and upon binding, disrupts the sperm membrane (pore formation that disintegrates the membrane) resulting in mitochondrial and ATP leakage. This electrostatic binding also causes cellular aggregation and creates gloms of multiple-sperm protamine complexes that disrupt targeting and speed.

Protamine is an arginine-rich, highly cationic peptide with a substantial positive charge throughout the molecule. As such, protamine has also been characterized as a broad-spectrum antimicrobial agent associated with membrane depolarization. Membrane depolarization is characterized by a rapid rise in the membrane potential that results in sodium channels opening on the cellular membrane, causing an influx of sodium ions [Catterall, 1986]. Alterations in the membrane potential affects cellular viability [Aspedon and Groisman, 1996]. As with spermatozoa, bacterial cells also carry a net negative charge, which is highly attractive to cationic peptides.

All constituents of the preferred embodiment are biocompatible: The atomic size of the halo fullerene derivatives would impart no effect on non-spermatozoa cells; olfactory aldehydes (bourgeonal) are naturally occurring in the female reproductive system; and the cationic peptide (protamine) selectively binds to negatively charged molecules or surfaces (spermatozoa), while not interacting with other neutral eukaryotic cell membranes.

Alternative embodiments may include the addition of poly-1-lysine (PLL), an FDA approved natural homopolymer, which has been shown to possess antimicrobial activity with low toxicity [Chenicheri et al., 2018]. Like protamine, PLL induces physiological damage to the negatively charged outer membrane of bacteria through potent electrostatic attraction [Chenicheri et al., 2018]. PLL also inhibits specific components of the electron transport system of mitochondria, which compromises cellular integrity through the generation of ROS [Symonds et al., 2005]. PLL is used routinely in sperm microscopy to inhibit motility during imaging; however, its presence is known to induce calcium fluxes in sperm [Wennemuth et al., 1998].

If included in the present invention, PLL may enhance binding; whereby, the PLL polymer and sperm membrane would impede movement, cause aggregation, disrupt membrane integrity and induce calcium fluxes in the sperm. Calcium fluxes across the membrane of spermatozoa play a critical role in various signal transduction pathways. As such, calcium is a well-known messenger that mediates the fertilization process, including activation of sperm motility, chemotaxis, hyperactivation, capacitation, and the acrosome reaction. Calcium regulates asymmetric movement of flagella, and the concentration of intracellular calcium must be precisely regulated to control targeting. PLL also inhibits electron transport systems that cause ROS production linked to capacitation initiation triggers. In the proposed invention, PLL would thus impede motility, damage structural components, and mimic fertilization cues typically produced when spermatozoa are in the accumulation zone (ovum proximity).

In another embodiment, hormones may also be added to enhance the contraceptive effect. For example, progesterone or analogues thereof, are well known to stimulate sperm hyperactivation—with a paradoxical reduction in progressive motility (reduced linearity) despite vigorous sperm movement. During fertilization, progesterone stimulates hyperactivation-like motility in the accumulation zone proximal to the ovum, enabling the sperm to dwell in this region.

The delivery methods for the contraceptive include a simple syringe and plunger or a rapidly dissolving suppository optimized for solubility at a neutral pH of 7, consistent with vaginal homeostasis. Post-coital exudates containing incapacitated spermatozoa, cellular and molecular particulates, halo fullerene aggregates, and stimulant analytes would remain neutral with respect to vaginal tissues to allow gravitational and normal vaginal secretions clearance. The exudate may also remove bacterial, fungal or viral debris, if present in the vagina and/or introduced during coitus and following biocidal rupture by the halo fullerenes.

Preferred Embodiment 1 a. A caustic halo fullerene (halogenated functionalized fullerenes) between 0.01% and 5.0%, preferably 0.1% and 1.5%, and in particular between 0.5% and 1.0% based on the total weight of the composition;
b. A highly cationic peptide (protamine) between 0.0001% and 1.0%, preferably 0.001% and 0.1%, and in particular 0.01% and 0.05% based on the total weight of the composition;
c. An aromatic aldehyde (bourgeonal) between 0.0001% and 2.0%, preferably 0.001% and 1.0%, and in particular 0.01% and 0.1% based on the total weight of the composition;

in a pH-neutral, buffered suspension that is inserted into the vagina prior to coitus.

Embodiment 2 a. A caustic halo fullerene (halogenated functionalized fullerenes) between 0.01% and 5.0%, preferably 0.1% and 1.5%, and in particular between 0.5% and 1.0% based on the total weight of the composition;
b. A highly cationic peptide (protamine) between 0.0001% and 1.0%, preferably 0.001% and 0.1%, and in particular 0.01% and 0.05% based on the total weight of the composition;
c. An aromatic aldehyde (bourgeonal) between 0.0001% and 2.0%, preferably 0.001% and 1.0%, and in particular 0.01% and 0.1% based on the total weight of the composition;

in a pH-neutral buffered suspension contained within a dissolvable suppository that is inserted into the vagina prior to coitus.

Embodiment 3 a. A caustic halo fullerene (halogenated functionalized fullerenes) between 0.01% and 5.0%, preferably 0.1% and 1.5%, and in particular between 0.5% and 1.0% based on the total weight of the composition;
b. A highly cationic peptide (protamine) between 0.0001% and 1.0%, preferably 0.001% and 0.1%, and in particular 0.01% and 0.05% based on the total weight of the composition;
c. An aromatic aldehyde (bourgeonal) between 0.0001% and 2.0%, preferably 0.001% and 1.0%, and in particular 0.01% and 0.1% based on the total weight of the composition;
d. A highly cationic polymer (poly-L-lysine) between 0.0001% and 1.0%, preferably 0.001% and 0.1%, and in particular 0.01% and 0.05% based on the total weight of the composition;

in a pH-neutral, buffered suspension that is inserted into the vagina prior to coitus.

Embodiment 4 a. A caustic halo fullerene (halogenated functionalized fullerenes) between 0.01% and 5.0%, preferably 0.1% and 1.5%, and in particular between 0.5% and 1.0% based on the total weight of the composition;
b. A highly cationic peptide (protamine) between 0.0001% and 1.0%, preferably 0.001% and 0.1%, and in particular 0.01% and 0.05% based on the total weight of the composition;
c. An aromatic aldehyde (bourgeonal) between 0.0001% and 2.0%, preferably 0.001% and 1.0%, and in particular 0.01% and 0.1% based on the total weight of the composition;
d. A highly cationic polymer (poly-L-lysine) between 0.0001% and 1.0%, preferably 0.001% and 0.1%, and in particular 0.01% and 0.05% based on the total weight of the composition;

in a pH-neutral buffered suspension contained within a dissolvable suppository that is inserted into the vagina prior to coitus.

Embodiment 5 a. A caustic halo fullerene (halogenated functionalized fullerenes) between 0.01% and 5.0%, preferably 0.1% and 1.5%, and in particular between 0.5% and 1.0% based on the total weight of the composition;
b. A highly cationic peptide (protamine) between 0.0001% and 1.0%, preferably 0.001% and 0.1%, and in particular 0.01% and 0.05% based on the total weight of the composition;

c. An aromatic aldehyde (bourgeonal) between 0.0001% and 2.0%, preferably 0.001% and 1.0%, and in particular 0.01% and 0.1% based on the total weight of the composition;
  d. A spermatozoa stimulating hormone (progesterone) between 1 nM and 100 μM, preferably 10 nM and 10 μM, and in particular 0.1 μM and 1 μM;

in a pH-neutral, buffered suspension that is inserted into the vagina prior to coitus.

Embodiment 6 a. A caustic halo fullerene (halogenated functionalized fullerenes) between 0.01% and 5.0%, preferably 0.1% and 1.5%, and in particular between 0.5% and 1.0% based on the total weight of the composition;
  b. A highly cationic peptide (protamine) between 0.0001% and 1.0%, preferably 0.001% and 0.1%, and in particular 0.01% and 0.05% based on the total weight of the composition;
  c. An aromatic aldehyde (bourgeonal) between 0.0001% and 2.0%, preferably 0.001% and 1.0%, and in particular 0.01% and 0.1% based on the total weight of the composition;
  d. A spermatozoa stimulating hormone (progesterone) between 1 nM and 100 μM, preferably 10 nM and 10 μM, and in particular 0.1 μM and 1 μM;

in a pH-neutral buffered suspension contained within a dissolvable suppository that is inserted into the vagina prior to coitus.

Embodiment 7 a. A caustic halo fullerene (halogenated functionalized fullerenes) between 0.01% and 5.0%, preferably 0.1% and 1.5%, and in particular between 0.5% and 1.0% based on the total weight of the composition;
  b. A highly cationic peptide (protamine) between 0.0001% and 1.0%, preferably 0.001% and 0.1%, and in particular 0.01% and 0.05% based on the total weight of the composition;
  c. An aromatic aldehyde (bourgeonal) between 0.0001% and 2.0%, preferably 0.001% and 1.0%, and in particular 0.01% and 0.1% based on the total weight of the composition;
  d. A highly cationic polymer (poly-L-lysine) between 0.0001% and 1.0%, preferably 0.001% and 0.1%, and in particular 0.01% and 0.05% based on the total weight of the composition;
  e. A spermatozoa stimulating hormone (progesterone) between 1 nM and 100 μM, preferably 10 nM and 10 μM, and in particular 0.1 μM and 1 μM;

in a pH-neutral, buffered suspension that is inserted into the vagina prior to coitus.

Embodiment 8 a. A caustic halo fullerene (halogenated functionalized fullerenes) between 0.01% and 5.0%, preferably 0.1% and 1.5%, and in particular between 0.5% and 1.0% based on the total weight of the composition;
  b. A highly cationic peptide (protamine) between 0.0001% and 1.0%, preferably 0.001% and 0.1%, and in particular 0.01% and 0.05% based on the total weight of the composition;
  c. An aromatic aldehyde (bourgeonal) between 0.0001% and 2.0%, preferably 0.001% and 1.0%, and in particular 0.01% and 0.1% based on the total weight of the composition;
  d. A highly cationic polymer (poly-L-lysine) between 0.0001% and 1.0%, preferably 0.001% and 0.1%, and in particular 0.01% and 0.05% based on the total weight of the composition;
  e. A spermatozoa stimulating hormone (progesterone) between 1 nM and 100 μM, preferably 10 nM and 10 μM, and in particular 0.1 μM and 1 μM;

in a pH-neutral buffered suspension contained within a dissolvable suppository that is inserted into the vagina prior to coitus.

Additional embodiments would include obvious combinations of the above-mentioned approaches or complementary molecules to those that have been proposed and as described in the specification of the patent. In particular, existing technology for dissolving capsules and matrices that provide vaginal lubrication for several days would represent another delivery mechanism for this contraceptive invention and would be apparent to those skilled in the art. This knowhow could provide a longer lasting contraceptive approach, as the halo fullerenes and other chemistries are not labile, suggesting routine, discreet administration for continuous efficacy, e.g. semi-weekly application in lieu of a requirement for use immediately before coitus. The various embodiments disclosed in this patent thus provide illustration, not limitations; the intended scope is therefore reflected in the following claims.

The invention claimed is:

1. A contraceptive composition that chemically stimulates, diverts targeting, impedes mobility, ruptures and incapacitates spermatozoa comprising:
  a. one or more halo fullerenes with the chemical formula of $C_{60}X_6$, $C_{60}X_8$, or $C_{60}X_{24}$, wherein X is a halogen selected from the group consisting of fluorine, chlorine, bromine, and iodine;
  b. bourgeonal;
  c. protamine;
  d. optionally one or more pharmaceutical-grade additives.

2. The composition of claim 1, wherein the concentration of halo fullerenes is between 0.01% and 5.0%, based on the total weight of the composition.

3. The composition of claim 1, wherein the concentration of bourgeonal is between 0.0001% and 2.0%, based on the total weight of the composition.

4. The composition of claim 1, wherein the concentration of protamine is between 0.0001% and 1.0%, based on the total weight of the composition.

5. The composition of claim 1, wherein the halo fullerenes structurally damage and rupture the distal flagellum of spermatozoa.

6. The composition of claim 1, wherein the composition stimulates hyperactivation of spermatozoa.

7. The composition of claim 1, wherein the composition stimulates competitive behavior between spermatozoa from the same or multiple sources.

8. The composition of claim 1, wherein the composition induces motility impediments, chemotactic stimulation, cellular membrane rupture, and subsequent neutralization of spermatozoa.

9. The composition of claim 1, wherein the composition provides incapacitation of spermatozoa.

10. The composition of claim 1, wherein the composition provides for topical contraception that is sperm stimulating, attracting, and spermicidal.

11. The composition of claim 1, wherein the composition caustically and physically ruptures the cellular membrane of spermatozoa and irreversibly incapacitates the sperm.

12. The composition of claim 1, wherein the composition causes irreversible damage for incapacitation and immobility of the spermatozoa in the presence of seminal and/or vaginal fluids.

13. The composition of claim 1, which further comprises one or more of Helional and an aliphatic ester.

14. The composition of claim 1, which further comprises one or more pharmaceutical grade, steroidal hormones at a concentration consistent with spermatozoa stimulation.

15. The composition of claim 1, further comprising a natural homopolymer.

16. The composition of claim 1, wherein the halo fullerenes are biocidal and neutralize bacterial, fungal and viral pathogens present in vaginal or seminal fluids.

17. The composition of claim 1, wherein the composition is a liquid suspension, or wherein the composition is contained inside of a soluble capsule.

18. The composition of claim 1, wherein the composition and post-coital exudates of incapacitated spermatozoa, cellular and molecular particulates, halo fullerene aggregates, and stimulant analytes remain neutral with respect to vaginal tissues to allow gravitational evacuation and normal vaginal secretions clearance.

19. The composition of claim 17, wherein the composition is a buffered suspension that prolongs retention of the contraceptive for continuous efficacy.

\* \* \* \* \*

UNITED STATES PATENT AND TRADEMARK OFFICE
CERTIFICATE OF CORRECTION

| | | |
|---|---|---|
| PATENT NO. | : 11,298,375 B2 | Page 1 of 1 |
| APPLICATION NO. | : 17/499223 | |
| DATED | : April 12, 2022 | |
| INVENTOR(S) | : Terry Earl Brady et al. | |

It is certified that error appears in the above-identified patent and that said Letters Patent is hereby corrected as shown below:

On the Title Page

Item (71) should read:
--Terry Earl Brady, The Valley (AI);
Anthony Lee Dellinger, Brown Summit, NC (US);
Melinda K. M. Goddard, The Valley (AI);
Kristen Dellinger, Brown Summit, NC (US)--

Item (72) should read:
--Terry Earl Brady, The Valley (AI);
Anthony Lee Dellinger, Brown Summit, NC (US);
Melinda K. M. Goddard, The Valley (AI);
Kristen Dellinger, Brown Summit, NC (US)--

Signed and Sealed this
Fourteenth Day of June, 2022

Katherine Kelly Vidal
*Director of the United States Patent and Trademark Office*